United States Patent [19]
Tebbutt

[11] Patent Number: 5,753,794
[45] Date of Patent: May 19, 1998

[54] INTERNAL COMBUSTION ENGINE HAVING OXYGEN SENSOR WITH REFERENCE CRITERION CALIBRATION

[75] Inventor: Iain John Tebbutt, Ashby De La Zouch, England

[73] Assignee: British Gas plc, London, England

[21] Appl. No.: 636,268

[22] Filed: Apr. 24, 1996

[30] Foreign Application Priority Data

May 18, 1995 [GB] United Kingdom ............. 9510086

[51] Int. Cl.$^6$ ............................................. G01M 15/00
[52] U.S. Cl. ........................... 73/23.31; 60/276; 123/703
[58] Field of Search ........................... 73/23.31, 23.32, 73/116, 117.3; 60/276; 123/672, 676, 697, 703; 219/494, 497

[56] References Cited

U.S. PATENT DOCUMENTS

| | | |
|---|---|---|
| 4,471,648 | 9/1984 | Uchida et al. |
| 4,938,196 | 7/1990 | Hoshi et al. |
| 4,958,611 | 9/1990 | Uchinami et al. |
| 5,148,795 | 9/1992 | Toshinari et al. |
| 5,214,267 | 5/1993 | Hoshi et al. |
| 5,279,145 | 1/1994 | Suzuki ............................. 73/23.32 |
| 5,445,796 | 8/1995 | Mori ............................... 73/31.06 |
| 5,539,258 | 7/1996 | Sutton et al. |
| 5,552,640 | 9/1996 | Sutton et al. |

FOREIGN PATENT DOCUMENTS

| | | |
|---|---|---|
| 0 068 321 | 1/1983 | European Pat. Off. |
| 37 15 461 | 11/1987 | Germany. |
| 38 02 051 | 8/1988 | Germany. |
| 0 482 366 | 4/1992 | Germany. |

*Primary Examiner*—Richard Chilcot
*Assistant Examiner*—Eric S. McCall
*Attorney, Agent, or Firm*—Oblon, Spivak, McClelland, Maier, & Neustadt, P.C.

[57] ABSTRACT

An internal combustion engine has an engine unit with an exhaust pipe comprising an oxygen sensor an electrical resistance heater in a bridge circuit having a control resistance and two fixed resistances RA and RB. For calibration the cell is initially operated in atmospheric air with an heater power control circuit supplying variable D.C. power output, under control of a microcontroller, to the bridge to vary the temperature of the sensor. When the sensor gives an electrical output of a predetermined reference value, this is observed by the microcontroller which varies the value of the control resistance to a calibrating value RC2 at which the bridge nulls. Then the microcontroller is instructed to adopt the operating mode and in accordance with its program the microcontroller sets the resistance value of the control resistance at the control value RC1 correlated by an operating function in the program with the calibrating value RC2. When the sensor is placed in the exhaust and a control comprising the microcontroller and the control circuit is operated, the bridge receives d.c. power from the control circuit to raise the temperature of the sensor until the equality $$\frac{RH}{RC1} = \frac{RA}{RB}$$

is satisfied. At satisfaction, the bridge nulls when the heater resistance RH has the value RH1. This is observed by the microcontroller which varies the power output of the control circuit to hold the temperature of the sensor substantially constant by maintaining the heater resistance at its value RH1.

15 Claims, 7 Drawing Sheets

INTERNAL COMBUSTION ENGINE HAVING OXYGEN SENSOR WITH REFERENCE CRITERION CALIBRATION

BACKGROUND OF THE INVENTION

This invention concerns an internal combustion engine, and in particular an internal combustion engine having an oxygen sensing or lambda cell in an exhaust duct from the engine.

The internal combustion engine may be used in a combined heat and power system, or to drive a vehicle. The engine may be a reciprocating engine. The fuel powering the engine may be fuel gas, for example natural gas.

For the reduction of noxious exhaust emissions, it is known to provide catalytic converter means, for example, a three-way catalytic converter, in the exhaust duct. An oxygen sensing or lambda cell comprising zirconia is provided in the duct to give an electrical output signal which is a function of the amount of oxygen in the exhaust gases. The amount of oxygen in the exhaust gases is a function of the ratio of combustion air to fuel supplied to the engine (hereafter called the air/fuel ratio). The ratio of combustion air (supplied to the engine) to the stoichiometric air requirement is defined as the lambda ratio or lambda. It is desirable to maintain the air/fuel ratio at substantially a predetermined value so that the value of lambda is approximately equal to 1 so that the nature of the products of combustion in the exhaust duct is not detrimental to the performance of the catalytic converter means. Thus it is known to provide control means to vary the supply of fuel to maintain the air/fuel ratio at substantially the desired value in response to variation in the output signal from the lambda cell.

Alternatively, for the reduction of noxious emissions, it is known to operate the internal combustion engine at high levels of excess combustion air known as lean burn operation. But above a certain level of excess air, poor combustion will result leading to misfiring of the fuel mixture, power reduction of the engine, and possible damage to the engine and equipment driven thereby. Thus it is necessary to maintain the air/fuel ratio at substantially a predetermined value to ensure the required emission levels in the exhaust gases without misfiring. A lambda cell may be used for this purpose supplying signals to control means controlling the air/fuel ratio.

Figure 5:
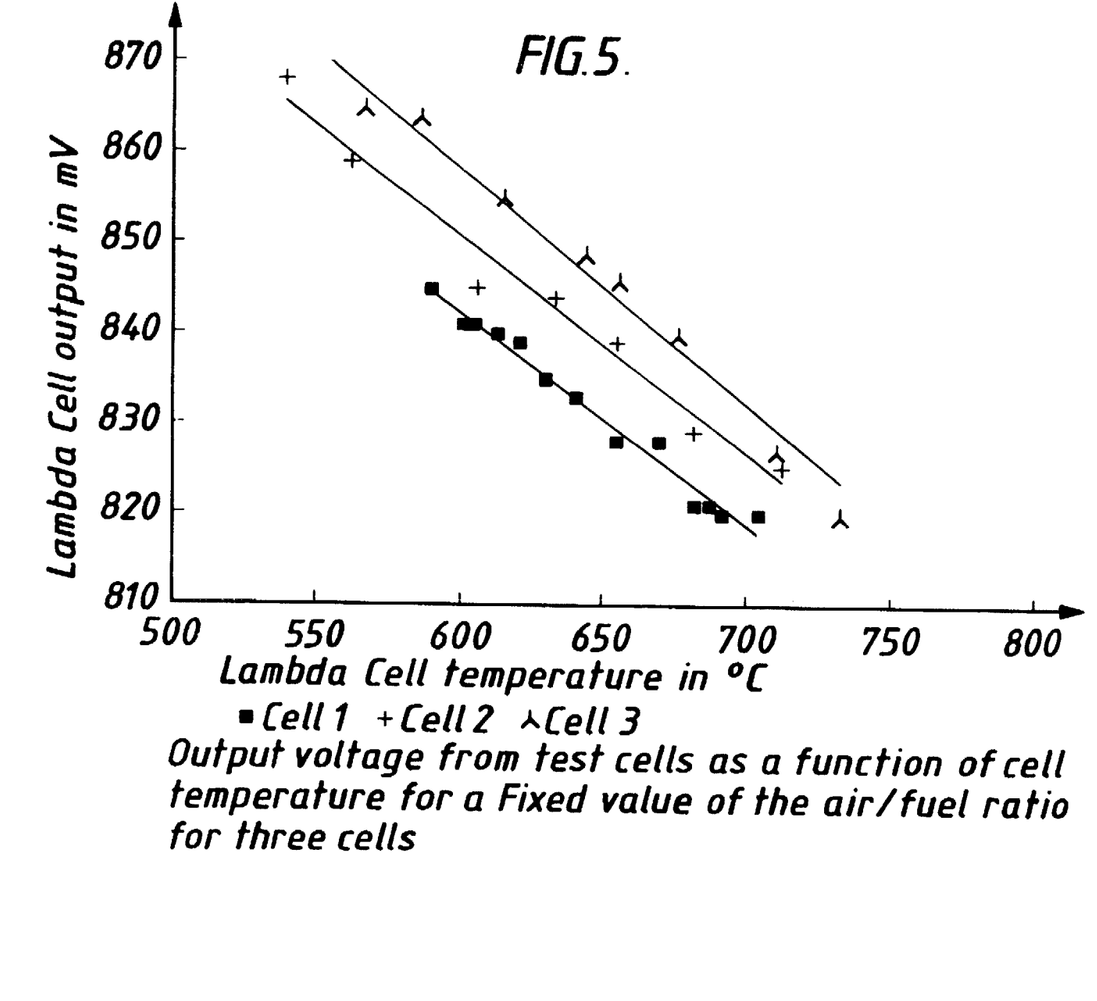
FIG. 5 is a number of graphs showing that for a fixed air/fuel ratio in the rich region (lambda less than 1), different zirconia lambda cells (of similar construction) observing the exhaust gas at the same place in an exhaust duct give different output voltages over similar temperature ranges.

Lambda cells comprising zirconia are not operated at ambient temperatures. They are provided with heating means, for example a metal heating coil which is electrically powered and has a resistance which increases with the temperature. The metal may be platinum. The idea is to try to and maintain the lambda cell at an operating temperature which, relatively speaking, is high, and not merely rely on the temperature of the exhaust gases passing a sensing element of the cell. Thus the cell temperature can be maintained high irrespective of the exhaust gas temperature. This is attempted by electrically powering the heating means. Unfortunately manufacturing tolerances mean that each lambda cell may be slightly different, so an uncontrolled electrical power supply will not be suitable to produce the appropriate heating of all cells. This causes difficulties when mass producing the internal combustion engines or when a lambda cell needs to be replaced. This is because the electrical output signal from a zirconia lambda cell is temperature dependent and also varies from cell to cell (see FIG. 5 hereof). Variations in the temperature of the cell cause variations in its electrical output signal in millivolts even though the cell may be observing exactly the same amount of oxygen. So if the lambda cell is operated at the wrong temperature, or if different cells are operated at the same temperature, the control means receives the electrical output signal representing an amount of oxygen different from that to which the cell(s) is/are actually exposed. As a consequence, the control means will regulate the air/fuel ratio to a wrong value which can reduce the effectiveness of noxious emissions reduction means whether that comprises the catalytic converter means or lean burn operation. In the lean burn case, unacceptable engine operation may also result.

An object of the invention is to provide an internal combustion engine so arranged that any lambda cell (having electrical heating means comprising electrical heating resistance means having a resistance value which varies as a function of temperature) used in the exhaust duct can be heated automatically to a correct temperature for that cell to give an electrical output having a value which accurately reflects the amount of oxygen observed by the cell.

SUMMARY OF THE INVENTION

According to the invention there is provided an internal combustion engine comprising an exhaust duct, an oxygen sensing or lambda cell provided in said duct, said cell comprising electrical heating means having a resistance value which varies as a function of temperature, control means to provide said heater means with electrical power to maintain said cell at a desired substantially constant operating temperature at which the heating means has a predetermined operating resistance value RH1, and said control means being arranged for making a comparison of the resistance value of the heating means with at least one reference criterion and for varying the electrical power in response to said comparison to maintain said cell at substantially said desired operating temperature; said reference criterion having been obtained from operation of the lambda cell whilst the cell is exposed to a reference gas comprising oxygen and the cell is simultaneously providing an electrical output signal having a value which is substantially a predetermined reference value.

Said reference gas may be the ambient atmospheric air.

BRIEF DESCRIPTION OF THE DRAWINGS

The invention will now be further described, by way of example, with reference to the accompanying drawings in which.

DETAILED DESCRIPTION OF PREFERRED EMBODIMENTS

Figures 1, 2:
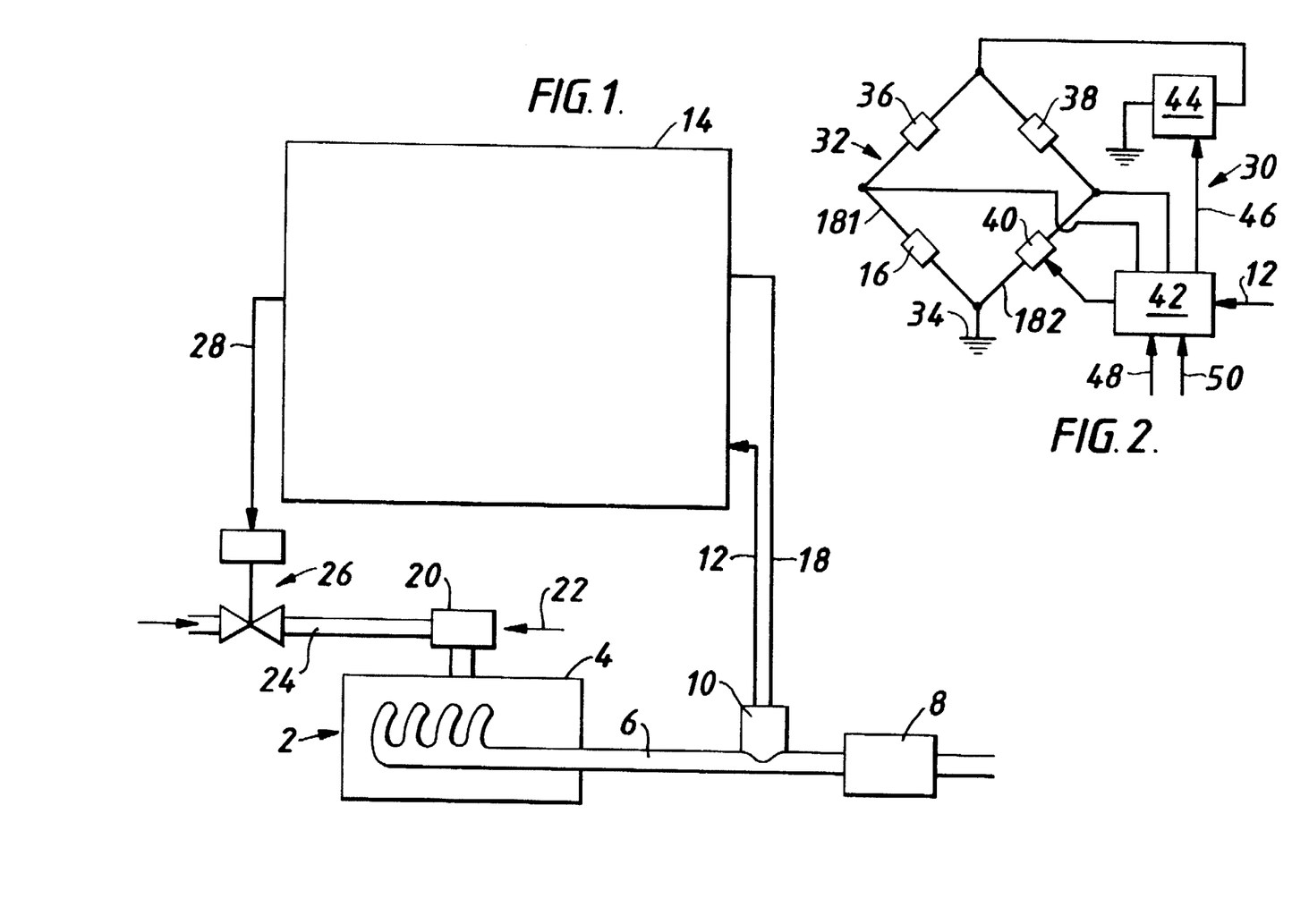
FIG. 1 is a diagrammatic illustration of an internal combustion engine formed according to the invention.
FIG. 2 diagrammatically illustrates a control system to maintain the lambda cell at a predetermined temperature, this system being included in the engine in FIG. 1.
Figure 3:
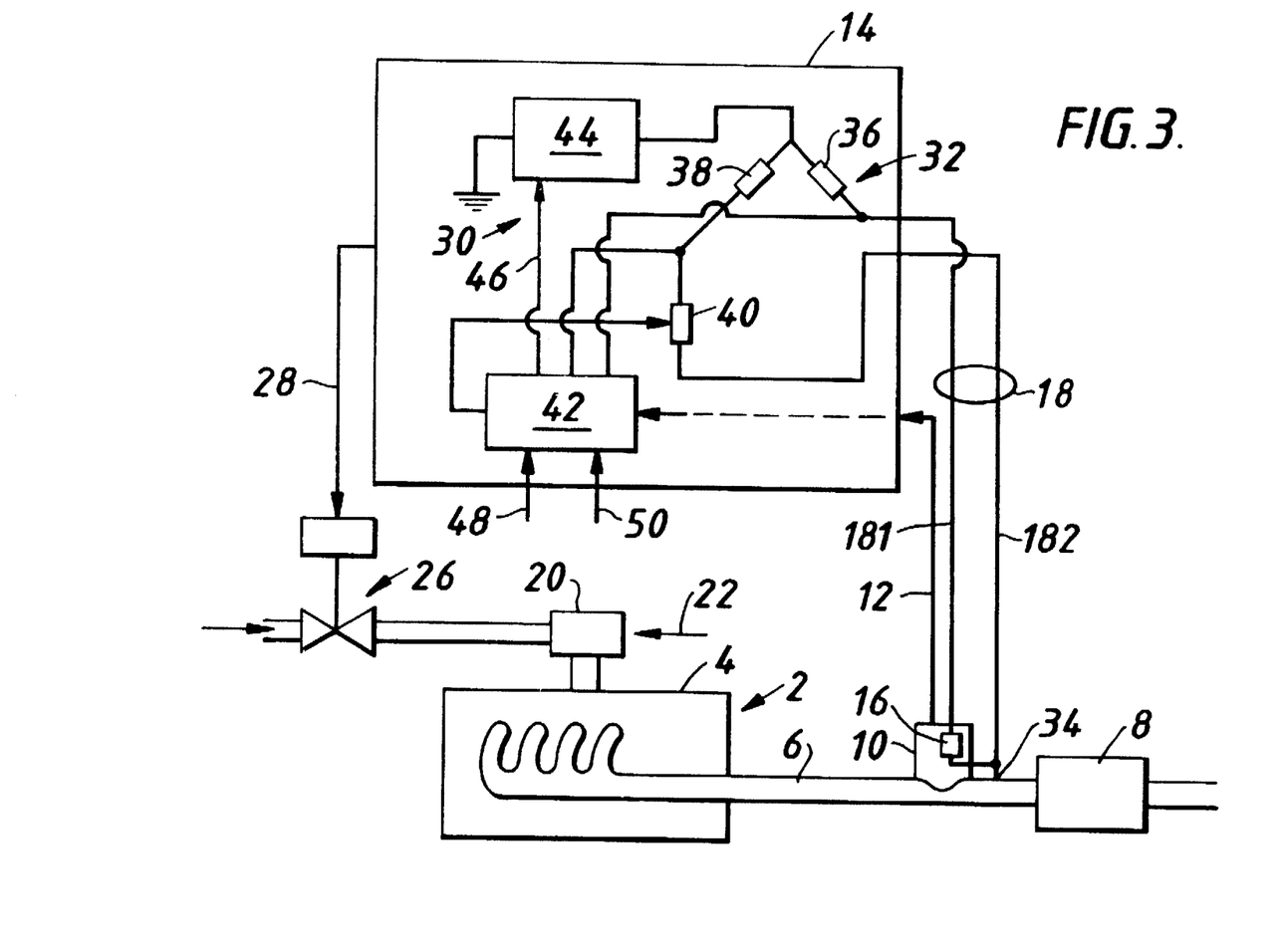
FIG. 3 shows the engine in FIG. 1 with the control system in FIG. 2 visually represented.

With reference to FIGS. 1 to 3, and in particular FIG. 1, a reciprocating internal combustion engine 2 has an engine unit 4 with an exhaust duct or pipe 6 comprising a catalytic converter 8. An oxygen sensor or lambda cell 10 is mounted in the exhaust pipe 6 upstream of the catalytic converter 8 and sends electrical voltage signals on signal path 12 to a control 14 comprising electronics. The lambda cell 10 can be of a zirconia type and includes an electrical heater or coil 16, for example a coil of platinum, having an electrical resistance which increases as its temperature increases. The lambda cell may be of a kind available from Bosch. Electrical power to energise the heater 16 is provided via cable 18 which, as shown in FIG. 3, comprises conducting paths 181 and 182. The engine 2 also includes a combustion air and fuel mixing and regulating device or carburettor 20 to which combustion air is supplied as indicated by arrow 22, and to which fuel gas, for example, natural gas, is supplied from a suitable supply along a duct 24 including a gas pressure control valve 26 which may be opened and closed electrically in response to signals, for example, electrical signals, on a signal path 28 and generated in the control 14 in response to signals received by the latter from path 12 from the lambda cell 10. In accordance with the signals from cell 10, the control in known manner operates the valve 26 to maintain the combustion air to fuel gas ratio supplied to the engine unit 4 substantially at a predetermined desired constant value.

Now with particular reference to FIGS. 2 and 3 the control 14 comprises a control system 30 comprising an electrical bridge 32 in one arm of which is the cell heater 16. The bridge 32 is grounded or earthed by, for example, being connected at 34 to the exhaust pipe 6. In the other arms of the bridge are fixed resistances 36 and 38 and a control resistance 40 having a value which is variable and set in known manner at a given value by a microcontroller 42 comprising computer means.

If the resistance values of the fixed resistances 36 and 38 are RA and RB respectively, then the bridge 32 nulls at $$\frac{RH1}{RA} = \frac{RC1}{RB} - (1).$$

Where RC1 (control value) is the resistance value of the control resistance 40, and RH1 is the operating resistance value of the heater 16 when the bridge nulls.

When equality (1) is re-arranged we see that the bridge 32 nulls when the ratio $\frac{RH1}{RC1}$ equals the fixed ratio $\frac{RA}{RB}$.

A heater control circuit 44 is under the control of the microcontroller 42 providing control signals on signal path 46. The heater control circuit 44 provides a d.c. electrical output to power the heater 16 having a resistance value which increases as the temperature of the heater increases until the resistance value of the heater reaches the operating value RH1 so that $$\frac{RH1}{RC1} = \frac{RA}{RB}.$$

When the microcontroller 42 observes the null point the electrical power output from the heater control circuit 44 is maintained substantially constant to keep the heater 16 at a desired operating temperature T1 (which is above the temperature of the exhaust gases in the pipe 6 passing the sensing element of the lambda cell 10) at which the resistance of the heater attains the operating value RH1. Should the temperature of the heater 16 now vary from the desired operating value T1 to increase or decrease the resistance value of the heater 16, departure from the null point is observed by the microcontroller 42 which causes the control circuit 44 to vary its power output by decreasing or increasing it to restore the resistance value of the heater 16 to the operating value RH1 (and thus restore the null point), so that the temperature of the cell 10 returns to the desired operating value T1.

The d.c. power output from the heater control circuit 44 may be varied by varying the d.c. voltage, or by providing the power output or electric current in square-wave form and varying the mark/space ratio thereof.

When the lambda cell 10 is operating at the desired operating temperature T1, which corresponds to the heater resistance value RH1, the cell is giving an electrical output signal which substantially accurately represents the amount of oxygen being observed by the cell, and thus can be relied on to cause the control 14 to operate the valve 26 to maintain the combustion air to fuel ratio supplied to the engine unit 4 at substantially the desired predetermined constant value.

The inventor has discovered that lambda cells 10 of the aforesaid type can be readily used, or substituted one for another, in the aforesaid control 14 if the control system 30 is appropriately calibrated. This is done by operating the lambda cell 10 in the ordinary or ambient atmospheric air outside the exhaust pipe 6, and with the microcontroller 42 operating in calibration mode. Calibration mode may be selected automatically in response to a signal to the microcontroller on signal path 48. The amount of oxygen in ordinary air may be assumed to be constant at about 20.9% by volume. Under control of the microcontroller 42 the heater control circuit 44 is operated to power the cell heater 16 to increase the temperature of the lambda cell 10 until the voltage of the output signal from the lambda cell reaches a predetermined reference value OV. When the microcontroller 42 observes the appearance of the voltage at the reference value OV the microcontroller 42 automatically operates to vary the value of the control resistance 40 and the electrical power supplied to the bridge 32 by the heater control circuit 44 until, with the lambda cell continuing to give an output voltage signal at the reference value OV, the microcontroller observes the null point of the bridge. At that null point the control resistance 40 has the resistance value RC2 (calibrating value), and the resistance of the heater 16 has the value RH2 which determines that the lambda cell 10 operates at a temperature T2 in the air to give the output reference voltage OV. The microcontroller 42 can note or record the calibrating value RC2 of the control resistance 40. The microcontroller 42 is programmed or otherwise provided with data defining an operating function or relationship by which any particular calibrating value RC2 of the control resistance 40 is correlated to a particular control value RC1 of the control resistance for when the lambda cell is to observe the exhaust gases. The operating function may be a linear function of the type $$RC2 = A \times RC1 + C \qquad (2),$$

where A and C are constants. Once a particular calibrating value RC2 is obtained, the microcontroller 42 derives the correlated control value RC1 upon receiving a signal on path 50 to automatically switch the microcontroller to operating mode in which the microcontroller changes the value of the control resistance 40 to the control value RC1, and the microcontroller is then ready to receive signals from the lambda cell 10 when positioned to observe the exhaust gases passing along the exhaust pipe 6.

Figure 7:
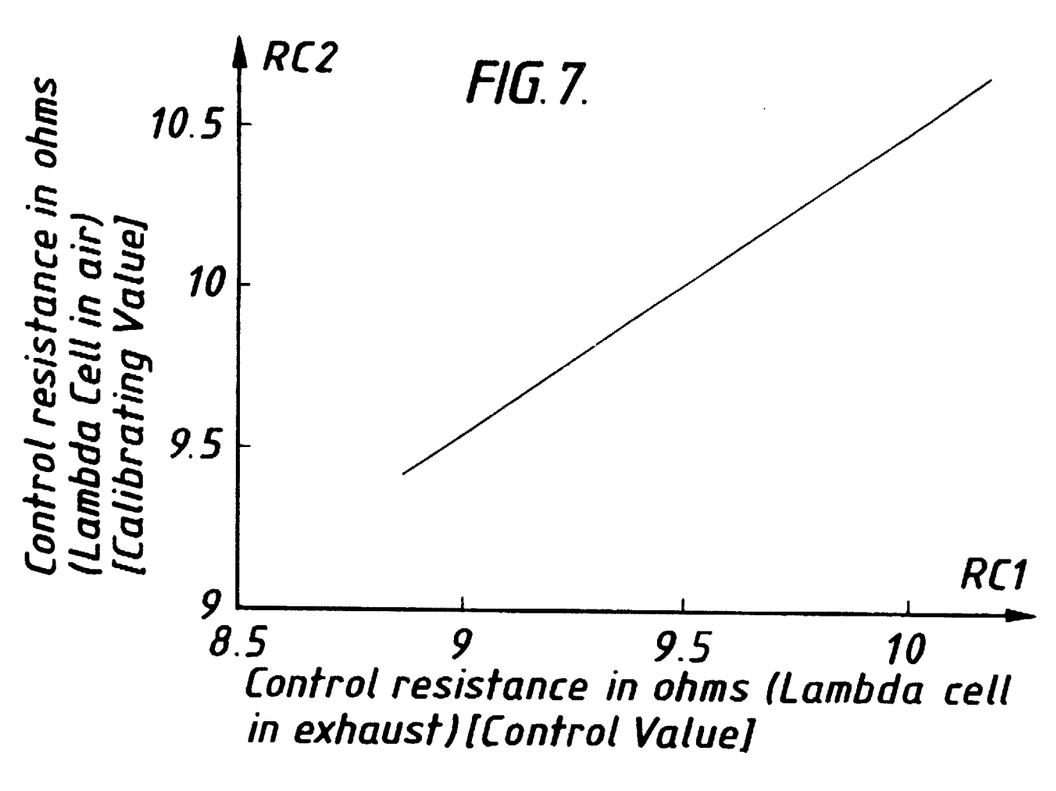
FIG. 7 is a graph showing a relationship used to determine at which resistance value the heating means of the lambda cell is to be operated, when the cell is observing oxygen in the exhaust gases, after the resistance value of the heating means has been measured whilst the lambda cell was observing the oxygen in atmospheric air and the heating means was at a temperature at which the cell gives a predetermined reference voltage output.

An example of the aforesaid operating function or relationship is represented by the graph in FIG. 7 by which calibrating resistance values for RC2 are correlated to control resistance values for RC1, so for any calibrating value for RC2 there is a particular value for RC1. The microcontroller 42 may calculate the control value for RC1 for any calibrating value for RC2 in accordance with the operating function or obtain the value for RC1 from previously derived look-up tables. With reference to the equation (2) above, in the operating function represented by FIG. 7, A is about 0.926 and C is about 1.221.

To determine the operating function or relationship by which calibrating resistance values RC2 are correlated to respective control resistance values RC1 a number of lambda cells 10 are mounted in the same exhaust pipe 6, at the same longitudinal position along the pipe, each cell being connected with its own respective bridge circuit 32. The engine is run to feed exhaust gases along the exhaust pipe, and the electrical power supplied to the heater 16 of each cell 10 is varied by varying the value of the control resistance 40 to control the operating temperature of the cell so that the output voltages from the cells are all substantially the same, say the voltage V1. Now the value of the control resistance 40 in each bridge 32 is observed. This gives the control value RC1 for each cell. Then with all the lambda cells 10 in air, the cells are again heated by application of electrical power to each cell which is varied by variation of the respective control resistance 40 until all the cells give the same predetermined output voltage OV. Now the value of the control resistance 40 in each bridge 32 is observed to give the control value RC2 for each cell so that each of the values for RC2 can be plotted against the corresponding value for RC1 to give the relationship as shown, by way of example, in FIG. 7, which we believe holds good for lambda cells as described above.

The predetermined output voltage reference value OV for the cell 10 operating in air (for calibration purposes) can be determined by trial and error as follows. The procedure described in the preceding paragraph was carried out using an arbitrarily chosen value for the output voltage OV, for example −10 mV. The correlation values of RC1 and RC2 were plotted and the degree to which a straight line relationship could be used for the correlation was noted. Further voltage values for OV were chosen and tests carried out to determine alternative values of RC2 for each cell. Further graphs were plotted of RC1 against RC2 for each output voltage value OV chosen. By examination of the degree of correlation and repetitive iteration of the output voltage value OV, a predetermined value OV for the output voltage is derived at which the straight line correlation of RC1 and RC2 values is deemed acceptable. We believe that a preferred value for the predetermined output voltage reference value OV is substantially −11.1 millivolts (mV).

Figure 4:
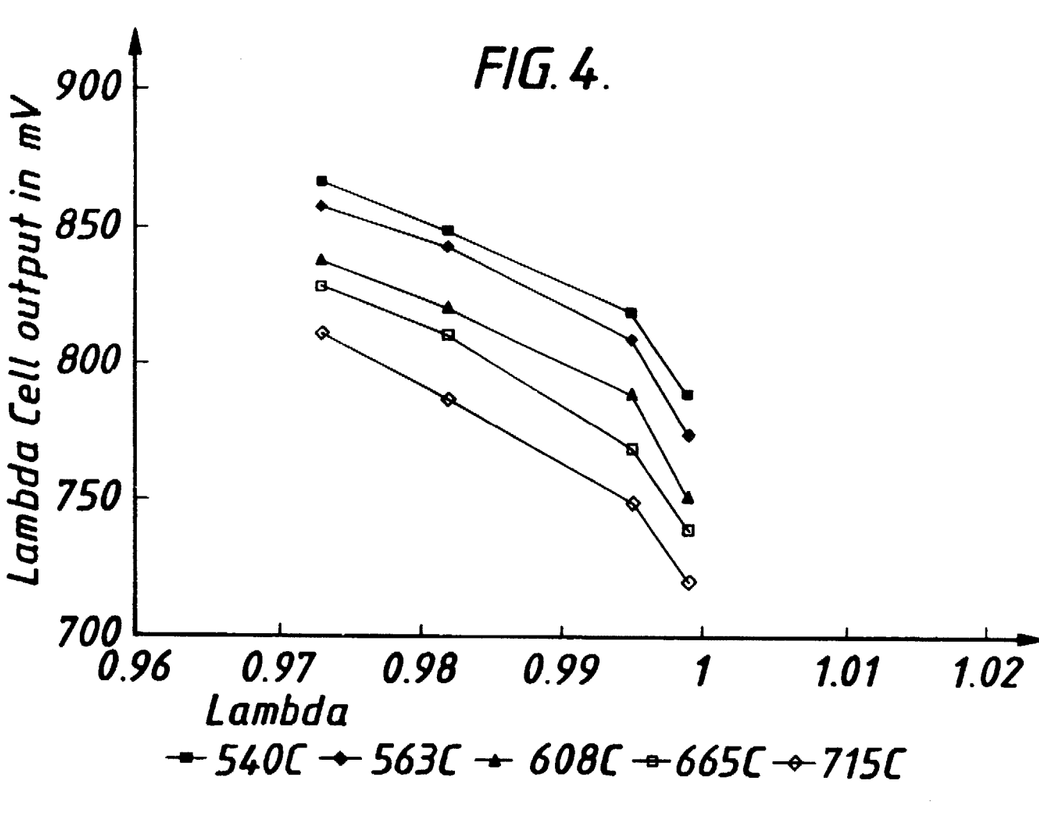
FIG. 4 is a number of graphs showing typical variation of a lambda cell output in millivolts plotted against variation in the lambda ratio or lambda when the cell is operated at temperatures 540, 563, 608, 665 and 715 degrees Celsius and the combustion air-fuel mixture supplied to the engine is rich.
Figure 6:
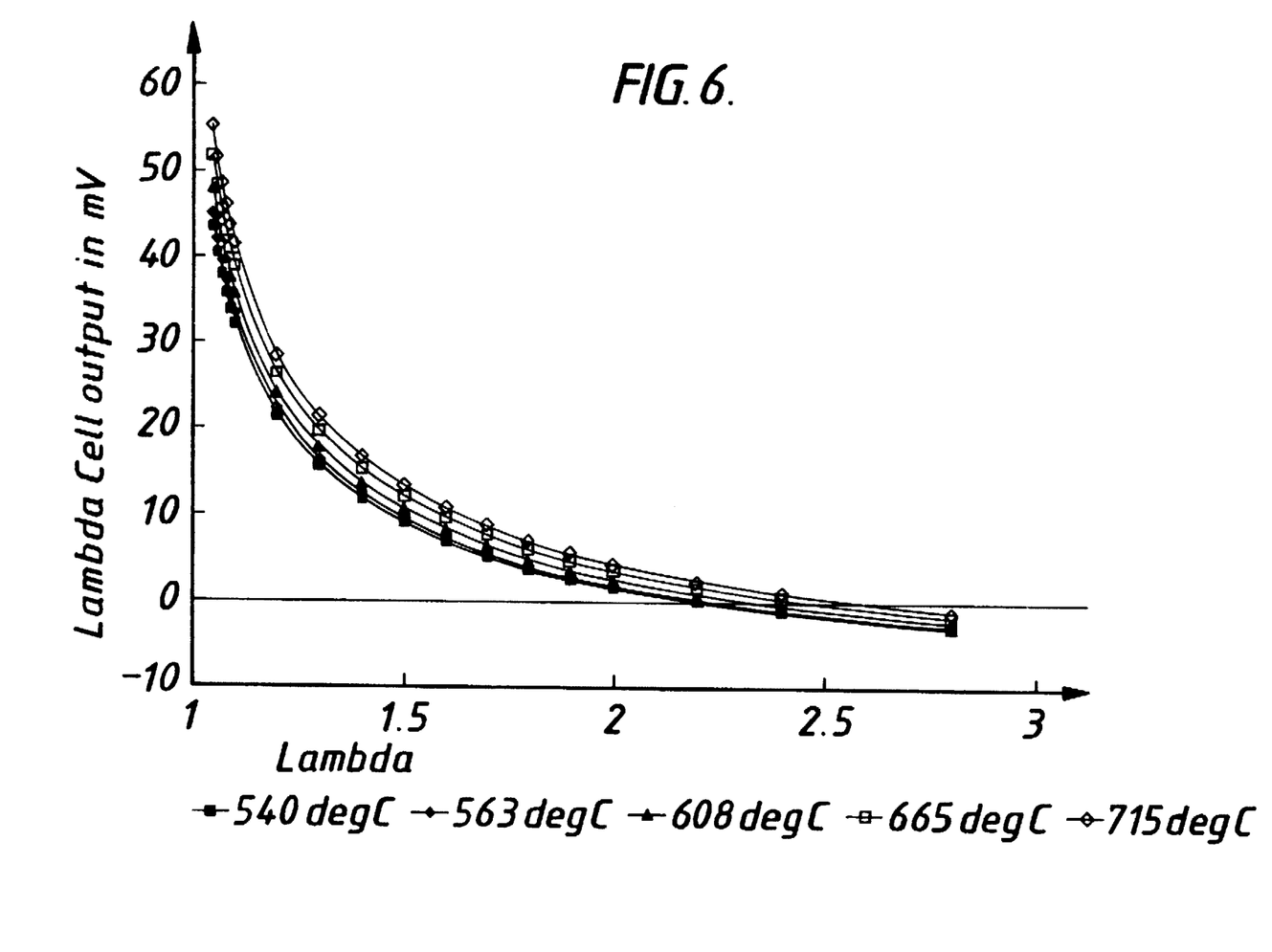
FIG. 6 is a number of graphs showing typical variation of the lambda cell output in millivolts plotted against variation in lambda when the cell is operated at the same temperatures as in FIG. 4 and the combustion air-fuel mixture supplied to the engine is lean.

With reference to FIGS. 4 and 6, the lambda cell output is a measure of oxygen in the exhaust gases when the engine is operating with a rich fuel mixture (lambda less than 1) and with a lean fuel mixture (lambda greater than 1). When the fuel mixture is rich, then for higher operating temperatures of the lambda cell the voltage output is lower for the same value of lambda. But the situation reverses above lambda equals 1 so that when the fuel mixture is lean then for higher operating temperatures of the lambda cell the voltage output is higher for the same value of lambda. We believe that by using the output reference voltage OV as described above to calibrate the bridge 32 for operation with any given lambda cell 10 of the type described to measure the oxygen in the exhaust gases, the operating temperature of any cell is at the appropriate desired temperature T1 for that cell, and the voltage output from the cell accurately reflects the amount of oxygen present in the exhaust whether the fuel and air mixture supplied to the engine unit is rich or lean.

Figure 8:
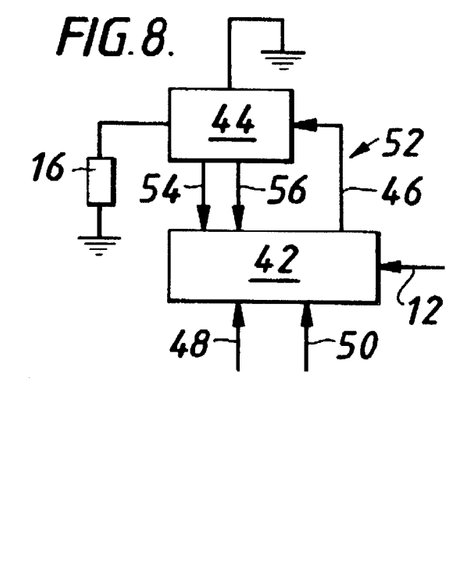
FIG. 8 diagrammatically illustrates another embodiment of the control system which may be used instead of the control system shown in FIGS. 2 and 3.

If desired, the control system 30 in FIGS. 2 and 3 can be substituted by a control system 52 in FIG. 8. The heater resistance 16 has a particular operating value RH1 at the desired lambda cell operating temperature T1. To maintain the lambda cell at the operating temperature T1 the resistance of the heater is maintained at the operating resistance value RH1. The microcontroller 42 controls the heater control circuit 44 to ensure that the electric power supplied to the heater 16 is sufficient to maintain the heater resistance at substantially the operating value RH1. The heater control circuit 44 can observe the values of the d.c. voltage across the heater 16 and the electric current supplied thereto and communicates these values to the microcontroller 42 by signals on signal paths 54 and 56 so that the microcontroller can calculate the resistance value of the heater 16 according to Ohm's law. Should that value vary from the desired operating value RH1, the power supplied to the heater 16 is varied to restore the heater resistance to the desired value RH1.

Figure 9:
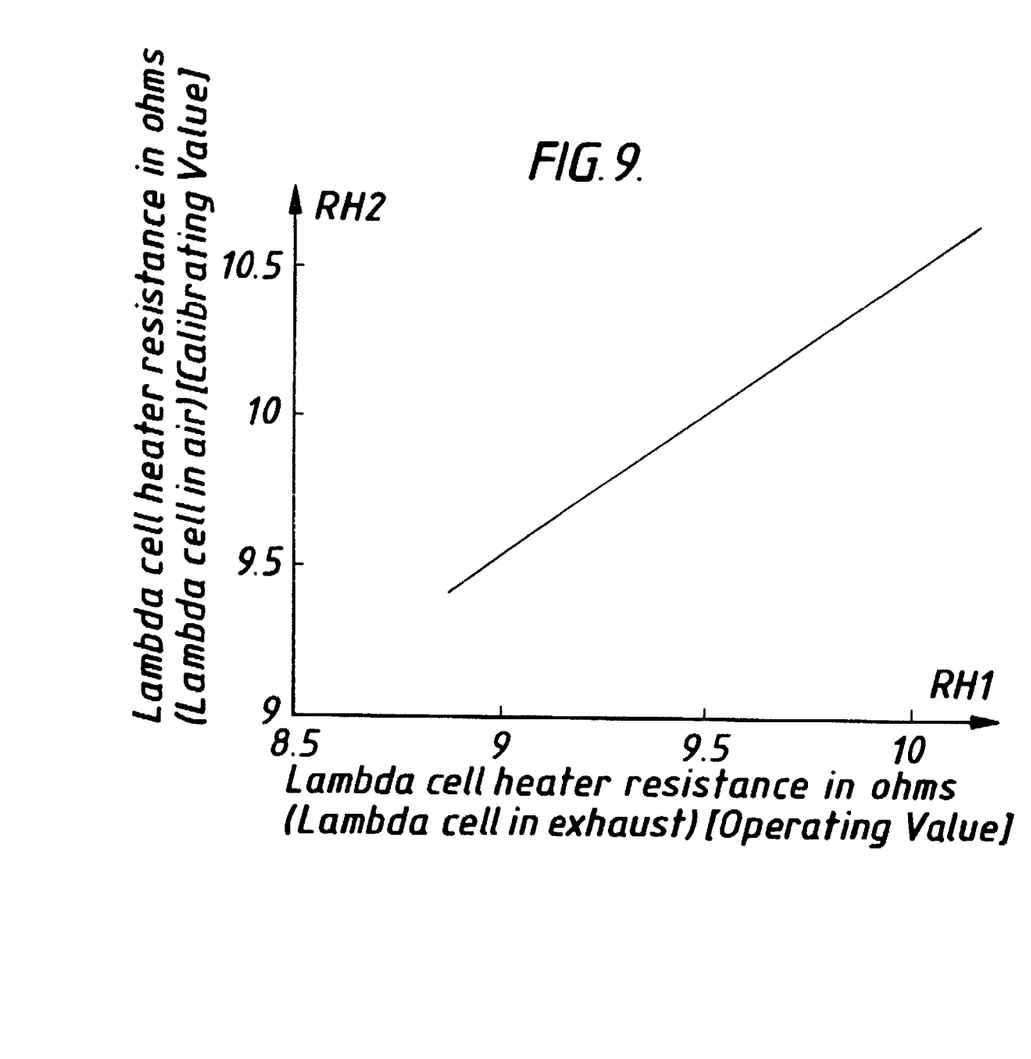
FIG. 9 is a graph similar to FIG. 7 in which the relationship therein is used by the control system in FIG. 8.

When the control system 52 is being calibrated in response to a signal on path 48 and the lambda cell is in air, the microcontroller 42 controls the operation of the heater control circuit 44 to vary the d.c. electrical power supplied thereto until the voltage signal having the predetermined reference value OV from the lambda cell is observed by the microcontroller as appearing on the signal path 12. At that point the microcontroller 42 calculates the resistance value RH2 of the heater 16 using the values of the voltage and current signals on paths 54 and 56 from the heater control circuit 44. The microcontroller 42 records or notes the calibrating resistance value RH2 and when switched to operating mode, by a signal on path 50, the microcontroller refers to the operating function or relationship, as represented in FIG. 9 for example, with which it is provided to determine the particular operating resistance value RH1 for the heater resistance correlated to the recorded calibrating value RH2. So that when the lambda cell is observing the exhaust gases the microcontroller 42 compares the resistance value of the heater 16 with the desired operating value RH1 and operates the heater control circuit 44 to ensure the heater 16 has the particular operating resistance value RH1. When a control system 52 is to be used in the control 14

(FIG. 1), a control system similar to the control system 30 with the bridge 32 may be used initially to discover the predetermined reference voltage value OV as described above. The control system 30 with the bridge 32 is also used to determine the operating function or relationship represented in FIG. 9, so that when the relationship in FIG. 7 is determined as described above one can simply substitute the calibrating values RH2 for RC2 (since they are the same) and also substitute the operating values RH1 for the values RC1 (since they are also the same) and hence obtain the operating relationship which the graph in FIG. 9 represents.

I claim:

1. An internal combustion engine comprising an exhaust duct, an oxygen sensing or lambda cell provided in said duct, said cell comprising electrical heating means having a resistance value which varies as a function of temperature, control means for providing said heater means with electrical power for maintaining said cell at a desired substantially constant operating temperature at which the heating means has a predetermined operating resistance value RH1, and said control means being arranged for making a comparison of the resistance value of the heating means with at least one reference criterion and for varying the electrical power in response to said comparison for maintaining said cell at substantially said desired operating temperature; said reference criterion having been obtained from operation of the lambda cell whilst the cell is exposed to a reference gas comprising a known concentration of oxygen and the cell is simultaneously providing an electrical output signal having a value which is substantially a predetermined reference value.

2. An internal combustion engine according to claim 1, wherein the reference gas is the ambient atmospheric air.

3. An internal combustion engine according to claim 1, wherein the lambda cell comprises zirconia and the heater means comprises a platinum heater.

4. An internal combustion engine according to claim 2, wherein the lambda cell comprises zirconia and the heater means comprises a platinum heater, and said predetermined reference value is substantially −11.1 millivolts.

5. An internal combustion engine according to claim 1 wherein a calibrating resistance value is obtained by operating the cell exposed to said reference gas whilst the cell is providing the output signal at substantially said reference value, and said control means comprises an operating function by which a control resistance value RC1 is correlated with said calibrating resistance value RC2, and wherein said control resistance value RC1 provides said reference criterion.

6. An internal combustion engine according to claim 5, wherein said control means comprises an electrical control resistance in one arm of an electrical bridge circuit and the heating means in another arm, said control resistance has a resistance value which is controllably variable to adopt said control resistance value RC1, and at the null point of said bridge $$\frac{RH1}{RC1} = K,$$

where K is a predetermined constant.

7. An internal combustion engine according to claim 6, wherein said control resistance is automatically variable for attaining said null point of the bridge circuit whilst the electrical power supplied to said heating means is variable to cause the resistance of said heating means to attain a value which is substantially equal to said operating resistance value RH1.

8. An internal combustion engine according to claim 6, wherein said control means comprises microcontroller means for controlling variation of said control resistance and variation of said electrical power supplied to said heating means.

9. An internal combustion engine according to claim 5, wherein said operating function is a substantially linear function of variation of the control resistance value with respect to variation of said calibration resistance value.

10. An internal combustion engine according to claim 1, wherein a calibrating resistance value RH2 is obtained by operating the cell exposed to said reference gas whilst the cell is providing the output signal at substantially said reference value, and said control means comprises an operating function by which the operating resistance value RH1 is correlated with said calibrating resistance value RH2, and said operating resistance value RH1 provides said reference criterion.

11. An internal combustion engine according to claim 10, wherein said reference criterion is stored in said control means, the control means can vary automatically the electrical power supplied to said heating means, and in response to data representing voltage across said heating means and electric current supplied to the heating means said control means can calculate the resistance of the heating means and vary the electrical power supplied in response to a difference between the calculated value and said reference criterion to cause the resistance of said heating means to attain a value which is substantially equal to said operating resistance value RH1.

12. An internal combustion engine according to claim 10, wherein the operating function is a substantially linear function of variation of the operating resistance value RH1 with variation of said calibrating resistance value RH2.

13. An internal combustion engine according to claim 1, fuelled by fuel gas.

14. An internal combustion engine according to claim 13, wherein the fuel gas is natural gas.

15. An internal combustion engine according to claim 1, included in one of a combined heat and power system and a vehicle.

* * * * *